United States Patent
Halder et al.

(10) Patent No.: US 9,983,154 B2
(45) Date of Patent: May 29, 2018

(54) METHOD FOR INSPECTING A PATTERN OF FEATURES ON A SEMICONDUCTOR DIE

(71) Applicant: IMEC VZW, Leuven (BE)

(72) Inventors: Sandip Halder, Bierbeek (BE); Philippe Leray, La Hulpe (BE)

(73) Assignee: IMEC VZW, Leuven (BE)

( * ) Notice: Subject to any disclaimer, the term of this patent is extended or adjusted under 35 U.S.C. 154(b) by 0 days. days.

(21) Appl. No.: 15/349,363

(22) Filed: Nov. 11, 2016

(65) Prior Publication Data

US 2017/0167992 A1 Jun. 15, 2017

(30) Foreign Application Priority Data

Dec. 14, 2015 (EP) .................................... 15199848

(51) Int. Cl.
*G01B 15/04* (2006.01)
*G01N 23/22* (2018.01)
*G01N 23/225* (2018.01)

(52) U.S. Cl.
CPC .......... *G01N 23/2251* (2013.01); *G01B 15/04* (2013.01); *G01N 2223/6116* (2013.01); *G01N 2223/646* (2013.01)

(58) Field of Classification Search
CPC .......... G06T 7/001; G06T 7/0006; G06T 7/30; G06T 7/0004; G06T 5/008; G06T 5/40; G06T 5/50; H01L 22/12; H01L 22/20; H01L 21/76897; H01L 21/76802; H01L 21/76807; H01L 21/67253; H01L 27/1463; H01L 27/14654; H01L 31/101; G01N 21/01; G01N 21/47; G01N 21/4785; G01N 21/88; G01N 21/8851; G01N 21/6501; G01N 21/956; G01N 23/20091; G01N 23/22; G01N 23/2251
(Continued)

(56) References Cited

U.S. PATENT DOCUMENTS 6,121,156 A * 9/2000 Shamble ........... H01L 21/76802
  257/687
6,185,324 B1 * 2/2001 Ishihara ................. G01N 21/88
  257/E21.525

(Continued)

FOREIGN PATENT DOCUMENTS

WO 2015/136533 A1 9/2015

*Primary Examiner* — David A Vanore
(74) *Attorney, Agent, or Firm* — McDonnell Boehnen Hulbert & Berghoff LLP

(57) ABSTRACT

The present disclosure is related to a method for detection of defects in a printed pattern of geometrical features on a semiconductor die, the pattern comprising an array of features having a nominal pitch, the method comprising determining deviations from the nominal pitch in the printed pattern, and comparing the printed pattern with another version of the pattern, the other version having the same or similar pitch deviations as the printed pattern. According to various embodiments, the other version of the pattern may a printed pattern on a second die, or it may be a reference pattern, obtained by shifting features of the array in a version having no or minimal pitch deviations, so that the pitch deviations in the reference pattern are the same or similar to the pitch deviations in the printed pattern under inspection.

20 Claims, 4 Drawing Sheets

(58) Field of Classification Search
USPC .................. 250/305, 307; 382/149, 145, 170
See application file for complete search history.

(56) References Cited

U.S. PATENT DOCUMENTS

| | | | |
|---|---|---|---|
| 6,301,008 B1 | 10/2001 | Ziger et al. | |
| 6,587,581 B1* | 7/2003 | Matsuyama | G01N 21/8851 |
| | | | 250/305 |
| 7,248,732 B2* | 7/2007 | Kuwabara | G06T 7/001 |
| | | | 356/237.4 |
| 8,036,447 B2* | 10/2011 | Hayakawa | G06T 7/001 |
| | | | 382/141 |
| 8,526,710 B2* | 9/2013 | Nakagaki | G06T 7/0006 |
| | | | 382/149 |
| 9,170,209 B1* | 10/2015 | Chang | G01N 21/9501 |
| 2002/0187582 A1* | 12/2002 | Satya | H01L 31/101 |
| | | | 438/48 |
| 2004/0190008 A1 | 9/2004 | Mieher et al. | |
| 2006/0280358 A1* | 12/2006 | Ishikawa | G01N 21/95607 |
| | | | 382/149 |
| 2008/0241970 A1* | 10/2008 | Winkler | H01L 21/67253 |
| | | | 438/5 |
| 2011/0311126 A1* | 12/2011 | Sakai | G01N 21/47 |
| | | | 382/149 |
| 2013/0140457 A1* | 6/2013 | Minekawa | G06T 7/0004 |
| | | | 250/307 |
| 2015/0176985 A1 | 6/2015 | Shchegrov et al. | |
| 2015/0233844 A1* | 8/2015 | Kohli | G01N 23/20091 |
| | | | 378/71 |
| 2015/0268164 A1* | 9/2015 | Amir | B05D 1/32 |
| | | | 356/243.1 |
| 2017/0167992 A1* | 6/2017 | Halder | G01N 23/2251 |

* cited by examiner

METHOD FOR INSPECTING A PATTERN OF FEATURES ON A SEMICONDUCTOR DIE

CROSS-REFERENCE TO RELATED APPLICATIONS

The present application is a non-provisional patent application claiming priority to European Patent Application No. EP 15199848.1, filed Dec. 14, 2015, the contents of which are hereby incorporated by reference.

FIELD OF THE DISCLOSURE

The present disclosure is related to the inspection of patterns of geometric features produced on a semiconductor die by lithography and etching.

BACKGROUND

Inspection of feature patterns produced by litho and etch technology is helpful in order to detect defects in the applied lithographic masks and/or process defects. Inspection tools are based on making comparisons between two dies on a single wafer, or between a die and a reference pattern.

Many chip designs comprise an array of longitudinal features placed parallel to each other at regular distances thereby defining an array with a given pitch. This may be for example an array of fin-shaped structures for making finFET devices on a memory chip. As the size of such features has decreased below the available resolution of immersion lithography, double patterning techniques such as LELE (Litho-Etch Litho-Etch) or SADP (Self-Aligned Double Patterning) have been developed which allow the production of these feature arrays down to the 14 nm technology node. One problem that is typical to these techniques is known as 'pitch walking': the pitch of an array of features is not constant between dies printed on the same wafer. For example for a half pitch of 24 nm in the designed pattern, the pitch may change from the center to the edge of the wafer from 24 to 30 nm. Inspection of such dies may lead to a failure to detect small defects because they are masked by the pitch walking error.

SUMMARY

The present disclosure is related to an inspection method as disclosed in the appended claims. The method helps avoid the negative impact of pitch errors.

The present disclosure is related to a method for detection of defects in a printed pattern of geometrical features on a semiconductor die, the pattern comprising an array of features having a nominal pitch, comprising the steps of: (1) determining deviations from the nominal pitch in the printed pattern, and (2) comparing the printed pattern with another version of the pattern, the other version having the same or similar pitch deviations as the printed pattern.

According to an embodiment, the semiconductor die is a first die of a plurality of dies comprising versions of the same printed pattern, and the method further comprises the step of determining deviations from the nominal pitch of the array in each of the plurality of dies, wherein the other version of the pattern is a pattern printed on a second die of the plurality of dies, the second die comprising an array with the same or similar pitch deviations as the first die. In some embodiments, the plurality of dies may be printed on the same semiconductor wafer.

According to an embodiment, an initial pattern is provided having no or minimal deviations from the nominal pitch of the array and the other version of the pattern is a reference pattern obtained by shifting one or more features of the array in the initial pattern, so that the pitch deviations in the reference pattern are the same or similar to the pitch deviations in the printed pattern. According to an embodiment, the initial pattern is a design intent pattern.

According to an embodiment, the semiconductor die is a first die of a plurality of dies, and the method further comprises the step of determining deviations from the nominal pitch of the array in each of the plurality of dies, wherein the initial pattern is a pattern produced on a second die of the plurality of dies, the second die comprising an array with minimal or no deviations from the nominal pitch.

In the latter embodiment, the plurality of dies may be printed on the same semiconductor wafer.

According to an embodiment, the deviations from the nominal pitch are determined by CD-SEM measurements.

The present disclosure is further related to a method for detection of defects in a plurality of dies printed on a semiconductor wafer, each die of the plurality of dies comprising a version of the same printed pattern of geometrical features, the pattern comprising one or more arrays of features having a nominal pitch, wherein deviations with respect to the nominal pitch are determined in each array of each die of the wafer, the method according to any one of the preceding paragraphs is applied to each of the plurality of dies, and if a second printed version of the pattern is used for the comparison step, the second version is a version printed on a second die of the wafer.

According to an embodiment, one or more of the defects are caused by misalignment of cut masks (10).

According to an embodiment, one or more of the defects are process defects or defects caused by errors in a lithographic mask.

DETAILED DESCRIPTION

The above-described pitch error problem and the negative consequences for defect detection are first described in more detail on the basis of the accompanying drawings. The upper and lower image of FIG. 1 respectively show a regular array of rectangular features 1-4, printed on two different die locations, in some examples printed on the same semiconductor wafer. The arrays are part of a larger pattern comprising a multitude of features. The same pattern may be printed on several die locations on the same wafer. The term 'printing' of the pattern is to be understood as a process comprising one or more exposures of a resist layer applied on the wafer, through a litho-mask, and developing the resist layer, so that the exposed areas of the resist become visibly distinct from non-exposed areas. In the case of the double patterning techniques referred to above, the printing includes additional steps according to the actual double patterning method applied, including steps which result in the realization of the final pattern on the die. The lithography tool can be any suitable known type of tool, such as a wafer stepper or a wafer scanner, wherein a pulsed laser beam is scanned through the mask and through a suitable lens assembly, illuminating portions of a die area as defined by the mask's pattern.

Figure 1:
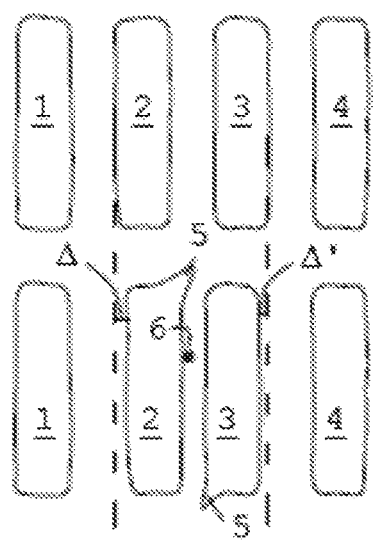
FIG. 1 illustrates a problem caused by pitch errors when comparing two printed versions of the same pattern.

The upper and lower image of FIG. 1 show the final pattern without and with pitch deviations respectively: in the lower image, the features 2 and 3 are shifted towards each other over distances Δ and Δ', whereas features 1 and 4 have remained virtually in the same place. 'Pitch deviations' may thus be defined in the present context as deviations from the pitch measured between each pair of neighboring features of the array. The pitch deviation is induced by the misplacement of the structure 2 towards structure 3. Because of this misplacement, the pitch between structure 2 and 1 is larger than intended. The pitch between structure 2 and 3 is proportionally smaller. The lower image is understood to be the pattern under inspection, to be inspected by comparison to the pattern of the upper image. Besides the pitch deviations, small defects 5 are present on features 2 and 3 in the pattern under inspection, for example due to inaccuracies in the lithographic mask used to print the features. Also a process defect 6 is visible in the pattern under inspection. This may be a particle of etched material that is left on the surface of the die after completion of an etching process.

Some example inspection tools for die-to-die comparison of the lower image of FIG. 1 to the upper image are based on image processing techniques. For example, an image is produced of the two arrays, possibly by performing a CD-SEM (Critical-Dimension Scanning electron microscopy) measurement and extracting from the results a contour of the printed features. The contours are then compared on a pixel-by-pixel basis, and a ranking of defects is made based on the difference between feature positions in the two compared images.

In the case of the arrays shown in the upper and lower image of FIG. 1, the pitch errors will show up high in the defect ranking, in such a manner that the mask defects 5 and the process defect 6 are either not detected or have a low probability of being detected.

Figure 2:
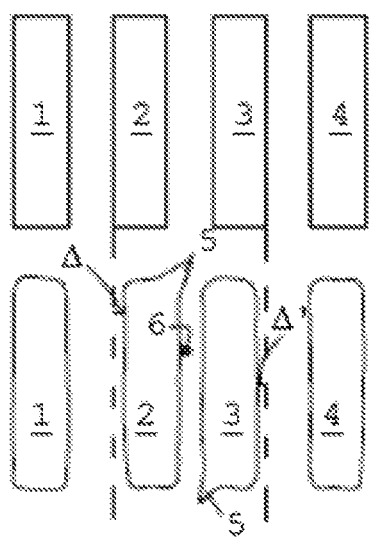
FIG. 2 illustrates a problem caused by pitch errors when comparing a printed pattern to a design intent pattern.

The same problem may occur when dies are compared to the design intent pattern, as illustrated in FIG. 2. The design intent is defined here as the theoretical pattern of features as designed. It is derivable for example from the Graphic Database System (GDS) file of a particular layer of the semiconductor die. The upper image of FIG. 2 shows the design intent of the array of features 1-4. As in the case of the direct comparison between two dies, the positional errors Δ and Δ' in the printed array in the lower image of FIG. 2 are likely to obstruct the detection of the litho-mask defects 5 and the process defect 6, when the printed array is compared to the design intent.

Some examples methods of the present disclosure help fix these problems by first determining the actual pitch deviations in an array of features on the die or dies under inspection. This can be done by a technique such as CD-SEM. For example, the distance between neighboring features in the array may be measured at regular intervals along the longitudinal direction of the features, and these measured values may be averaged to result in the average distance between each pair of neighboring features. The pitch deviation can be measured with CD-SEM taking into account a proper anchoring before the measurement, i.e. determining a reference point with respect to which the position of the features is determined. The anchoring can be based on an additional feature used to do pattern recognition. This anchoring ensures the identification and positioning of a structure to start with (structure 1 for example). Any deviation of the position of feature 1 from the reference position is then to be taken into account when determining the pitch deviations.

From these measurements, the pitch deviations can be found between each pair of neighboring features of the array, by comparing the measured pitch with the nominal pitch. The nominal pitch of a regular array of features is the pitch as defined by the design intent pattern. So the nominal pitch is one single number for a particular array, defining, for example, the distance between the center lines of two neighboring features of the array.

In some examples, the pattern under inspection is then compared to another version of the same pattern, having an array with the same or similar pitch deviations as the pattern under inspection. The comparison may result in a defect ranking. Because arrays are compared which have the same or similar pitch deviations, these pitch deviations are no longer dominating the defect ranking, and smaller defects, such as the mask defects 5 and process defect 6 are more likely to be detected. At the same time, the pitch deviations as such are detected because of the preliminary measurement of these deviations. The method therefore allows for detecting pitch deviations caused by pitch walking, for example, while at the same time allowing for the detection of smaller mask or process defects.

According to a first embodiment, the 'other version' of the pattern is a printed pattern printed on the same wafer as the pattern under inspection. In some examples, the pitch deviations are measured in the above-described way for a plurality of dies printed on a single wafer. The wafer may for example be a focus and dose modulated test wafer, on which a plurality of versions of the same pattern are printed under varying conditions of the de-focus and dose of the lithography tool. Dies printed at a given de-focus value may then be compared to dies printed at zero de-focus, in order to establish a process window for the tool's focus settings.

According to the first embodiment, the pattern of a particular die under inspection can be compared only to the pattern on a second die with the same or similar pitch deviations as the die under inspection. For example when pitch walking increases from the center of the wafer to the edge of the wafer, dies near the edge are consistently compared to dies that are also near the edge, so that the pitch walking error between compared dies is similar.

Figure 3:
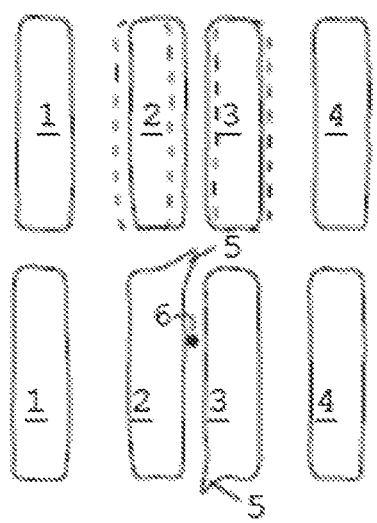
FIG. 3 illustrates an example method when applied to inspection by die-to-die comparison.

As illustrated in FIG. 3, when the array under inspection (lower image) is compared to an array that has the same pitch error (upper image), the mask defects 5 and the process defect 6 are higher in the defect ranking, because the pitch error is not detected as such.

Figure 4:
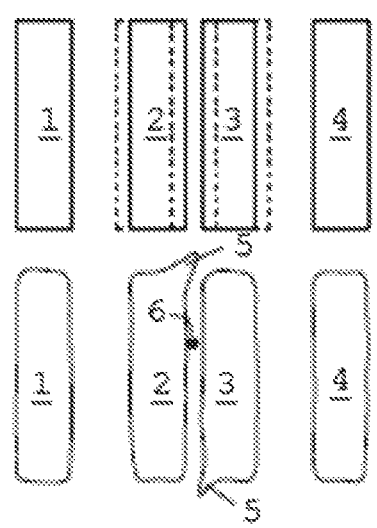
FIG. 4 illustrates an example method when applied to inspection by comparison of a printed die to a design intent pattern.

Instead of comparing the pattern to a pattern printed on another die with similar pitch error, the pattern may be compared to a reference pattern, obtained by starting from an initial pattern having no or minimal pitch errors in the array, and shifting the features of the array, so that the pitch deviations in the reference pattern become the same or similar to the pitch deviations observed in the die under inspection. The initial pattern may be the design intent pattern, wherein the features of the array or arrays are shifted so as to correspond with the pitch deviations observed in the pattern under inspection. This approach is illustrated in FIG. 4. The upper image shows the design intent, but with features 2 and 3 shifted to right and left respectively, so as to correspond to the pitch deviations observed in the pattern under inspection shown in the lower image. Comparison of the upper and lower images again increases the ranking of the defects 5 and 6.

Figure 5:
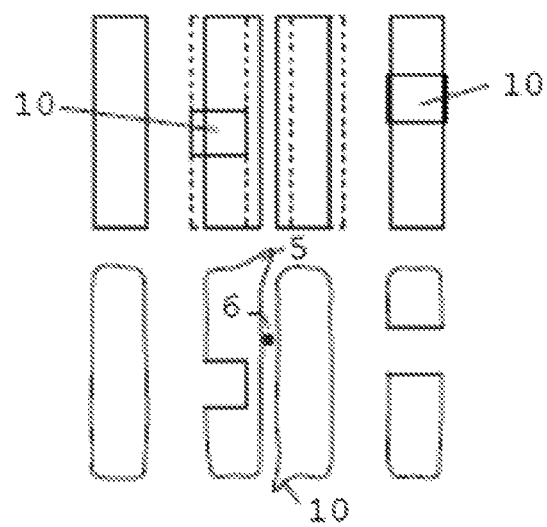
FIG. 5 illustrates a defect caused by misalignment of cut masks.

FIG. 5 illustrates another type of defect that is more likely to be detected by the method of the present disclosure. When cut masks 10 are used to interrupt the rectangular features of an array 1-4, these cut masks are well aligned with the design intent, but when a pitch deviation occurs in the printed features, the cut mask is misaligned with one or more of the features, resulting in features that are not fully cut, as shown in FIG. 5. These errors are also likely to go undetected unless the comparison is made with a second die or with a reference pattern that has the same or similar pitch deviation as the die under inspection.

The reference pattern may be obtained by shifting features in the design intent pattern as described above. Alternatively, the reference may be obtained by shifting features in an actual pattern printed on a die. For example, when the array 1-4 is printed on one die with no or minimal pitch error, this printed array may be used as the initial pattern, wherein the features on the array in this initial pattern are shifted according to the measured pitch errors on the die under inspection.

Figure 6:
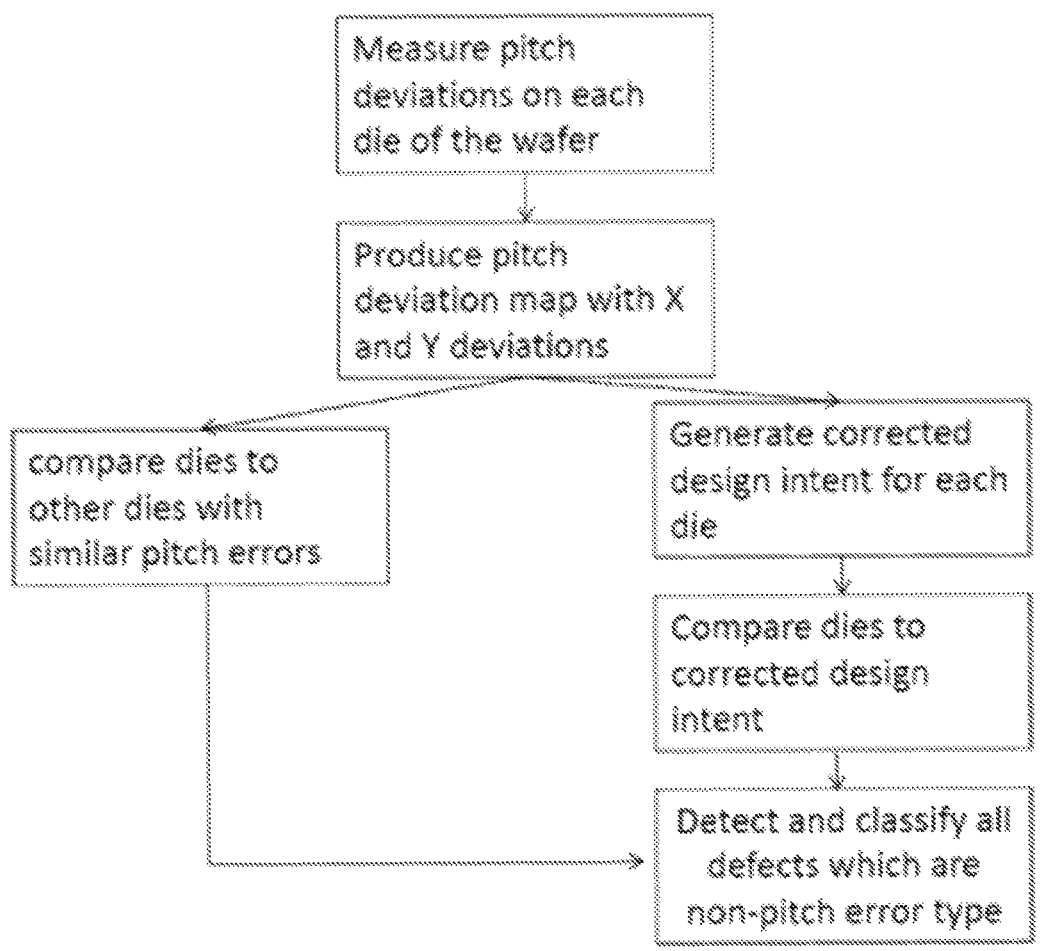
FIG. 6 shows a flow diagram of an example method of the present disclosure, when applied to a wafer comprising multiple dies.

FIG. 6 shows the flow diagram of some embodiments of the present disclosure applied to the inspection of multiple dies printed on the same wafer, wherein the same pattern of features is printed on each die, the pattern comprising one or more arrays of features having a given pitch according to the design intent. Arrays may be arranged in one of two orthogonal directions X and Y. In a first step, the pitch errors are measured on each die (e.g. by CD-SEM) and a wafer map is made of X and Y deviations for each die on the wafer, i.e. these are the deviations of each feature of each array of the pattern, with respect to the arrays as they were designed according to the design intent. A choice can then be made between inspection based on die-to-die comparison and an inspection based on die-to-reference comparison. In the first case, only comparisons are made between dies which have the same or similar X and Y deviations for one or more of the arrays under inspection. This process may be automated by an algorithm that selects dies for comparison based on the X and Y deviations from the wafer map. It may for example be included in the algorithm that a comparison can only be made if the X or Y deviation is smaller than a given maximum.

In the second case (die-to-design intent), the design intent is adapted before each comparison is made, by shifting one or more of the features in the arrays on the design intent pattern according to the recorded X and Y deviations, so that these arrays have the same pitch deviations as the arrays under inspection in each die. Optionally, a third option may be provided (not shown), in which a die is first selected in which for one or more arrays the pitch deviations are minimum. The shift operation is then performed on contours of printed features of this die prior to each comparison. This third option is therefore identical to the die-to-design intent option, except that an actually printed die is used instead of the design intent, as the starting point before effectuating the shifts.

While examples have been illustrated and described in detail in the drawings and foregoing description, such illustration and description are to be considered illustrative or exemplary and not restrictive. Other variations to the disclosed embodiments can be understood and effected by those skilled in the art in practicing the claims, from a study of the drawings, the disclosure and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used. Any reference signs in the claims should not be construed as limiting the scope.

The invention claimed is:

1. A method for detection of one or more defects in a printed pattern of geometrical features on a semiconductor die, the printed pattern comprising an array of geometrical features having a nominal pitch, the method comprising:
   determining one or more deviations from the nominal pitch in the printed pattern; and
   comparing the printed pattern with a second version of the printed pattern, wherein the second version has the same or similar pitch deviations as the printed pattern.

2. The method according to claim 1, wherein the semiconductor die is a first die of a plurality of dies comprising versions of the same printed pattern, the method further comprising:
   determining deviations from the nominal pitch of the array in each of the plurality of dies, and wherein the second version of the printed pattern is a pattern printed on a second die of the plurality of dies, the second die comprising an array with the same or similar pitch deviations as the first die.

3. The method according to claim 2, wherein the plurality of dies are printed on the same semiconductor wafer.

4. The method according to claim 1, wherein an initial pattern is provided having no or minimal deviations from the nominal pitch of the array and wherein the second version of the printed pattern is a reference pattern obtained by shifting one or more features of the array in the initial pattern, such that pitch deviations in the reference pattern are the same or similar to pitch deviations in the printed pattern.

5. The method according to claim 4, wherein the initial pattern is a design intent pattern.

6. The method according to claim 4, wherein the semiconductor die is a first die of a plurality of dies, the method further comprising the step of determining one or more deviations from the nominal pitch of the array in each of the plurality of dies, and wherein the initial pattern is a pattern produced on a second die of the plurality of dies, the second die comprising an array with minimal or no deviations from the nominal pitch.

7. The method according to claim 6, wherein the plurality of dies are printed on the same semiconductor wafer.

8. The method according to claim 1, wherein the one or more deviations from the nominal pitch are determined by CD-SEM measurements.

9. The method of according to claim 1, wherein the nominal pitch is an average distance between center points of neighboring geometrical features of the printed pattern.

10. The method of according to claim 1, wherein the nominal pitch is an average distance between center points of neighboring geometrical features of a design intent pattern of the printed pattern.

11. The method according to claim 1, wherein determining one or more deviations from the nominal pitch in the printed pattern comprises determining both X direction and Y direction deviations.

12. The method according to claim 1, wherein the one or more defects in the printed pattern of geometrical features comprise mask defects or process defects.

13. The method according to claim 1, wherein the one or more defects are caused by misalignment of cut masks.

14. The method according to claim 1, wherein the one or more defects are process defects or mask defects.

15. A method for detection of defects in a plurality of dies printed on a semiconductor wafer, each die of the plurality of dies comprising a version of a printed pattern of geometrical features, the printed pattern comprising one or more arrays of features having a nominal pitch, the method comprising:
    determining, for each of the plurality of dies, one or more deviations from the nominal pitch in the printed pattern; and
    comparing, for each of the plurality of dies, the printed pattern with a second version of the printed pattern, wherein the second version has the same or similar pitch deviations as the printed pattern.

16. The method according to claim 15, wherein the second version of the printed pattern is printed on a second die of the semiconductor wafer.

17. The method according to claim 15, wherein an initial pattern is provided having no or minimal deviations from the nominal pitch of the one or more arrays, and wherein the second version of the printed pattern is a reference pattern obtained by shifting one or more features of the one or more arrays in the initial pattern, such that pitch deviations in the reference pattern are the same or similar to pitch deviations in the printed pattern.

18. The method according to claim 17, wherein the initial pattern is a design intent pattern.

19. The method according to claim 15, wherein the one or more deviations from the nominal pitch are determined by CD-SEM measurements.

20. The method according to claim 15, wherein the nominal pitch is an average distance between center points of neighboring geometrical features of the printed pattern.

* * * * *